US011903669B2

(12) United States Patent
Cope et al.

(10) Patent No.: US 11,903,669 B2
(45) Date of Patent: Feb. 20, 2024

(54) STERILE DRAPE FOR ROBOTIC DRIVE

(71) Applicant: Corindus, Inc., Newton, MA (US)

(72) Inventors: Jason Cope, Natick, MA (US); Peter Falb, Hingham, MA (US); Bruno Piazzarolo, Waltham, MA (US); Wayne Boucher, Manchester, NH (US)

(73) Assignee: Corindus, Inc, Newton, MA (US)

( * ) Notice: Subject to any disclaimer, the term of this patent is extended or adjusted under 35 U.S.C. 154(b) by 0 days.

(21) Appl. No.: 17/813,626

(22) Filed: Jul. 20, 2022

(65) Prior Publication Data

US 2023/0034024 A1 Feb. 2, 2023

Related U.S. Application Data

(60) Provisional application No. 63/203,785, filed on Jul. 30, 2021.

(51) Int. Cl.
*A61B 46/10* (2016.01)
*A61B 34/30* (2016.01)
*A61B 90/50* (2016.01)
*A61B 17/00* (2006.01)

(52) U.S. Cl.
CPC .............. *A61B 46/10* (2016.02); *A61B 34/30* (2016.02); *A61B 90/50* (2016.02); *A61B 2017/00477* (2013.01)

(58) Field of Classification Search
CPC .... A61B 2017/00477; A61B 2034/301; A61B 34/30; A61B 46/10; A61B 90/50; A61M 2025/0042; A61M 25/0113; A61M 25/09041; A61M 25/10
See application file for complete search history.

(56) References Cited

U.S. PATENT DOCUMENTS

| | | | |
|---|---|---|---|
| 3,821,525 | A | 6/1974 | Eaton et al. |
| 5,312,338 | A | 5/1994 | Nelson et al. |
| 5,350,101 | A | 9/1994 | Godlewski |
| 6,436,107 | B1 | 8/2002 | Wang et al. |
| 6,697,664 | B2 | 2/2004 | Kienzle et al. |
| 7,331,967 | B2 | 2/2008 | Lee et al. |
| 7,766,856 | B2 | 8/2010 | Ferry et al. |
| 7,766,894 | B2 | 8/2010 | Weitzner et al. |
| 7,886,743 | B2 | 2/2011 | Cooper et al. |

(Continued)

FOREIGN PATENT DOCUMENTS

| | | |
|---|---|---|
| CN | 205514900 U | 8/2016 |
| CN | 206651871 U | 11/2017 |

(Continued)

OTHER PUBLICATIONS

European Search Report for Corresponding Application No. 22187207.0, dated Dec. 15, 2022.

(Continued)

*Primary Examiner* — Scott Luan

(57) ABSTRACT

A sterile barrier for a robotic drive comprises a first drive module configured to move moving along a longitudinal axis of a drive body. The sterile barrier comprises a first resilient member having a first free edge proximate the longitudinal axis. The first free edge adjacent the first drive module is resiliently biased away from and returned to the longitudinal axis as the first drive module moves along the longitudinal axis.

19 Claims, 13 Drawing Sheets

(56) References Cited

U.S. PATENT DOCUMENTS

| | | | |
|---|---|---|---|
| 7,947,050 B2 | 5/2011 | Lee et al. |
| 7,972,298 B2 | 7/2011 | Wallace et al. |
| 8,052,636 B2 | 11/2011 | Moll et al. |
| 8,092,397 B2 | 1/2012 | Wallace et al. |
| 8,220,468 B2 | 7/2012 | Cooper et al. |
| 8,343,096 B2 | 1/2013 | Kirschenman et al. |
| 8,617,102 B2 | 12/2013 | Moll et al. |
| 8,684,952 B2 | 4/2014 | Weitzner et al. |
| 8,708,952 B2 | 4/2014 | Cohen et al. |
| 8,720,448 B2 | 5/2014 | Reis et al. |
| 8,736,212 B2 | 5/2014 | Sandhu et al. |
| 8,801,661 B2 | 8/2014 | Moll et al. |
| 8,986,246 B2 | 3/2015 | Foley et al. |
| 9,283,046 B2 | 3/2016 | Walker et al. |
| 9,326,822 B2 | 5/2016 | Lewis et al. |
| 9,408,669 B2 | 8/2016 | Kokish et al. |
| 9,782,564 B2 | 10/2017 | Zirps et al. |
| 9,814,864 B2 | 11/2017 | Scarpine et al. |
| 9,820,751 B2 | 11/2017 | Haines et al. |
| 9,825,455 B2 | 11/2017 | Sandhu et al. |
| 10,010,699 B2 | 7/2018 | Cohen et al. |
| 10,213,264 B2 | 2/2019 | Tanner et al. |
| 10,307,214 B2 | 6/2019 | Lathrop et al. |
| 10,433,925 B2 | 10/2019 | Shelton et al. |
| 10,485,621 B2 | 11/2019 | Morrissette et al. |
| 10,603,126 B2 | 3/2020 | Karguth et al. |
| 10,743,956 B2 | 8/2020 | Pecora |
| 10,881,477 B1 | 1/2021 | Genova et al. |
| 10,881,478 B1 | 1/2021 | Genova et al. |
| 2001/0022109 A1 | 9/2001 | Wenninger et al. |
| 2002/0177789 A1 | 11/2002 | Ferry et al. |
| 2004/0254566 A1 | 12/2004 | Plicchi et al. |
| 2007/0060879 A1 | 3/2007 | Weitzner et al. |
| 2008/0243064 A1 | 10/2008 | Stahler et al. |
| 2009/0082722 A1 | 3/2009 | Munger et al. |
| 2012/0071752 A1 | 3/2012 | Sewell et al. |
| 2014/0276389 A1 | 9/2014 | Walker |
| 2015/0142013 A1 | 5/2015 | Tanner et al. |
| 2015/0202009 A1 | 7/2015 | Nussbaumer et al. |
| 2017/0007343 A1 | 1/2017 | Yu |
| 2017/0151024 A1 | 6/2017 | Deboeuf et al. |
| 2017/0348060 A1 | 12/2017 | Blacker |
| 2018/0200014 A1 | 7/2018 | Bonny et al. |
| 2018/0289438 A1 | 10/2018 | Pennoyer |
| 2019/0053866 A1 | 2/2019 | Seow et al. |
| 2019/0175887 A1 | 6/2019 | Shameli |
| 2019/0223965 A1 | 7/2019 | Marshall et al. |
| 2020/0069389 A1 | 3/2020 | Morrissette et al. |
| 2020/0163728 A1 | 5/2020 | Dalpe et al. |
| 2020/0188050 A1 | 6/2020 | Pennoyer et al. |
| 2020/0360095 A1 | 11/2020 | Grant et al. |
| 2021/0031007 A1 | 2/2021 | Alexander et al. |
| 2021/0121260 A1 | 4/2021 | Genova et al. |
| 2021/0177536 A1 | 6/2021 | Genova et al. |

FOREIGN PATENT DOCUMENTS

| | | | | |
|---|---|---|---|---|
| CN | 109091226 | | 12/2018 | |
| CN | 210408600 | | 4/2020 | |
| EP | 2124800 | | 11/2010 | |
| EP | 3033032 | | 6/2016 | |
| EP | 2335635 | | 7/2016 | |
| EP | 3103409 | | 12/2016 | |
| EP | 3119315 | | 1/2017 | |
| GB | 2538230 | | 11/2016 | |
| JP | 2008025684 | | 2/2008 | |
| JP | 2008025684 A * | 2/2008 | .............. F16C 29/08 |
| JP | 2020028775 | | 2/2020 | |
| JP | 2020028775 A * | 2/2020 | ............. A61B 34/30 |
| WO | 2009092059 | | 7/2009 | |
| WO | 2010067437 | | 6/2010 | |
| WO | WO-2010067437 A1 * | 6/2010 | ............. B60N 2/071 |
| WO | 2016194263 | | 12/2016 | |
| WO | 2016210111 | | 12/2016 | |
| WO | WO-2016194263 A1 * | 12/2016 | ....... A61B 17/00234 |
| WO | 2017158263 | | 9/2017 | |
| WO | 2018013236 | | 1/2018 | |
| WO | 2020141517 | | 7/2020 | |
| WO | 2020198027 | | 10/2020 | |
| WO | 2021011518 | | 1/2021 | |
| WO | 2021011533 | | 1/2021 | |
| WO | 2021011551 | | 1/2021 | |
| WO | 2021011554 | | 1/2021 | |
| WO | 2021011571 | | 1/2021 | |
| WO | 2022154975 | | 7/2022 | |
| WO | 2022154976 | | 7/2022 | |
| WO | 2022154977 | | 7/2022 | |
| WO | 2022154978 | | 7/2022 | |
| WO | 2022154980 | | 7/2022 | |

OTHER PUBLICATIONS

Mori H, Koshida K, Ishigamori O, Matsubara K. A novel removable shield attached to C-arm units against scattered X-rays from a patient's side. Eur Radiol. Aug. 2014;24(8):1794-9. doi: 10.1007/s00330-014-3186-x. Epub May 2, 2014. PMID: 24788230.

Gershkovich GE, Tiedeken NC, Hampton D, Budacki R, Samuel SP, Saing M. A Comparison of Three C-Arm Draping Techniques to Minimize Contamination of the Surgical Field. J Orthop Trauma. Oct. 2016;30(10):e351-6. doi: 10.1097/BOT.0000000000000619. PMID: 27124823.

Al-Shawi AK, Fern ED. The tent drape for the C-arm image intensifier. Injury. Sep. 2004;35(9):927-9. doi: 10.1016/S0020-1383(03)00120-7. PMID: 15302249.

Biswas D, Bible JE, Whang PG, Simpson AK, Grauer JN. Sterility of C-arm fluoroscopy during spinal surgery. Spine (Phila Pa 1976). Aug. 1, 2008;33(17):1913-7. doi: 10.1097/BRS.0b013e31817bb130. PMID: 18622356.

Peters PG, Laughlin RT, Markert RJ, Nelles DB, Randall KL, Prayson MJ. Timing of C-arm drape contamination. Surg Infect (Larchmt). Apr. 2012;13(2):110-3. doi: 10.1089/sur.2011.054. Epub Mar. 22, 2012. PMID: 22439783.

1 Extended European Search Report for Corresponding Application No. 22187207.0, dated Mar. 20, 2023.

* cited by examiner

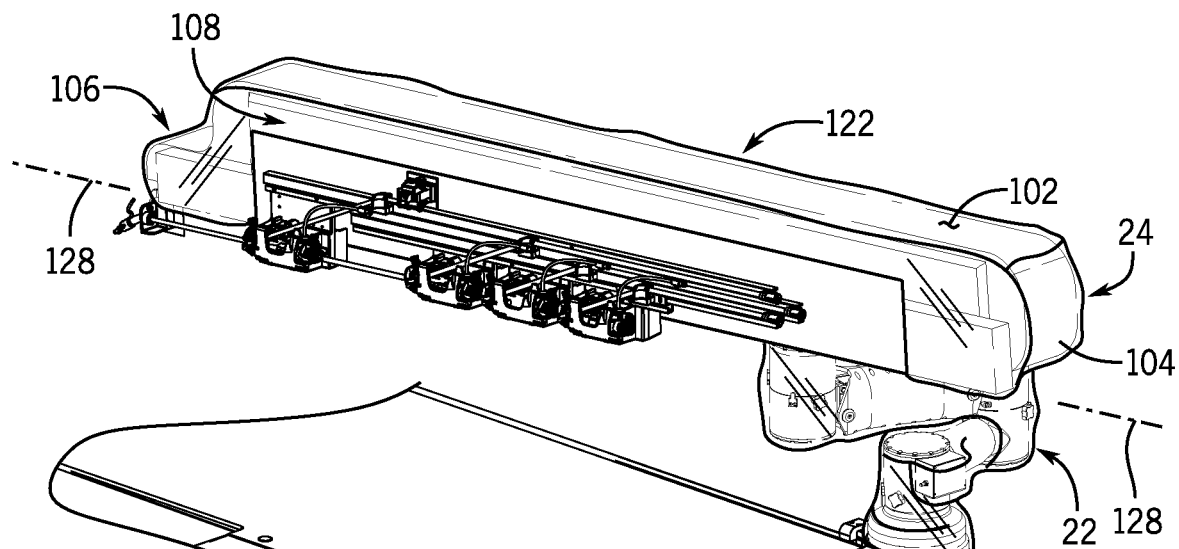
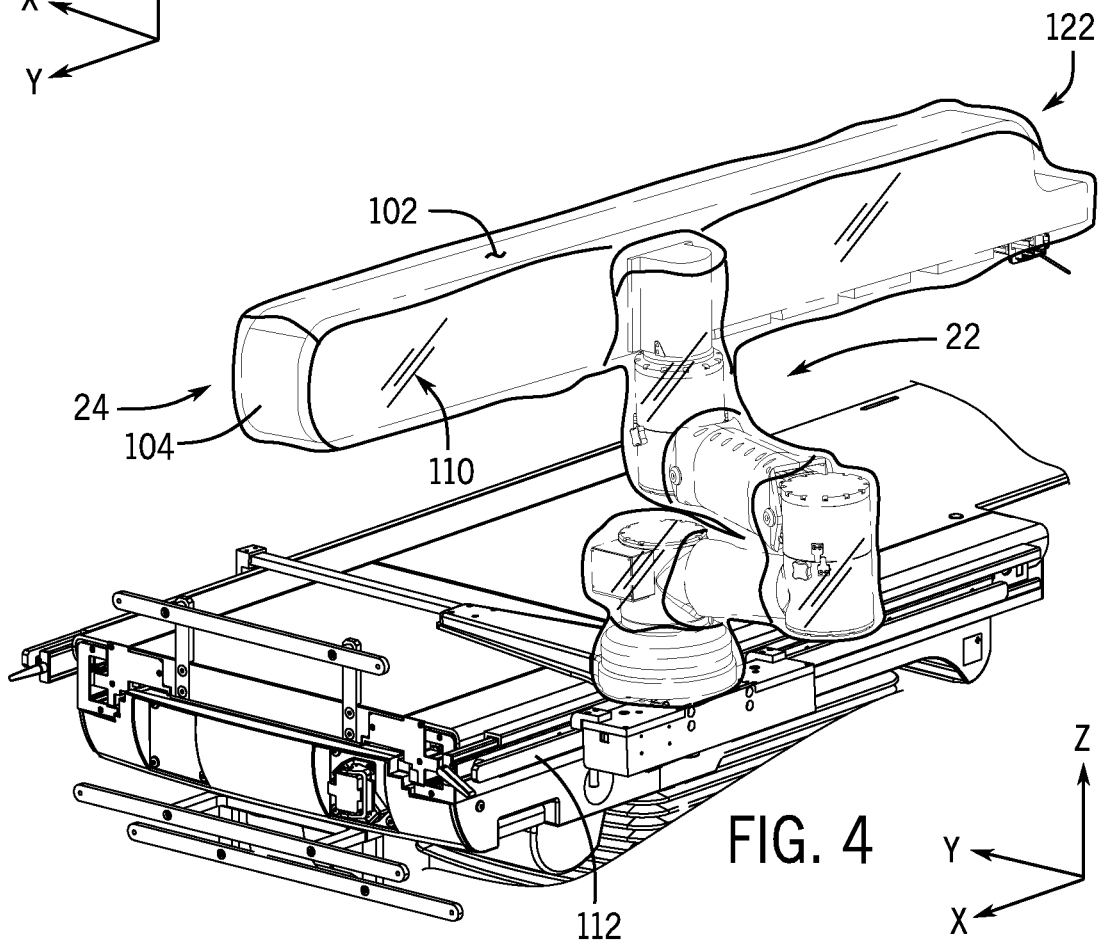

STERILE DRAPE FOR ROBOTIC DRIVE

CROSS-REFERENCE TO RELATED PATENT APPLICATIONS

This application claims benefit of U.S. Provisional Application No. 63/203,785 filed on Jul. 30, 2021, entitled STERILE DRAPE FOR ROBOTIC DRIVE, which is incorporated herein by reference in its entirety.

FIELD

The present invention relates generally to the field of robotic medical procedure systems and, in particular, to a drape system for separating a non-sterile portion of a robotic drive from a sterile portion of the robotic drive.

BACKGROUND

Catheters and other elongated medical devices (EMDs) may be used for minimally-invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters. The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

SUMMARY

In accordance with an embodiment a sterile barrier for a robotic drive comprises a first drive module configured to move moving along a longitudinal axis of a drive body. The sterile barrier comprises a first resilient member having a first free edge proximate the longitudinal axis. The first free edge adjacent the first drive module is resiliently biased away from and returned to the longitudinal axis as the first drive module moves along the longitudinal axis.

In one implementation the sterile barrier includes a second resilient member having a second free edge proximate the longitudinal axis, wherein the second free edge adjacent the first drive module resiliently is biased away from and returned to the longitudinal axis as the first drive module moves along the longitudinal axis between the first resilient member and the second resilient member.

In one implementation the sterile barrier includes a first rigid member removably coupled to the drive body wherein the first resilient member is secured to the first rigid member.

In one implementation the sterile barrier includes a flexible drape connected to the first rigid member, the flexible drape covering the drive body.

In one implementation the sterile barrier includes a first arm drape member having a C shaped clip removably secured to a portion of an arm supporting the drive body, the first arm drape including a lower arm drape being positioned under the arm, and wherein the flexible drape includes an upper arm drape section covering an upper portion of the arm, wherein the first arm drape member and the upper arm drape section cover an entire surface of the arm.

In one implementation the sterile barrier includes a second rigid member removably coupled to the drive body wherein the second resilient member is secured to the second rigid member.

In one implementation the first rigid member includes at least two sections that are in a folded orientation in a packaged configuration and an unfolded orientation in an install configuration.

In one implementation the first resilient member includes a first side and an opposing second side, the first side facing the drive body.

In one implementation the first side of first resilient member includes a first side and an opposing second side, a portion of the first side contacting an outer surface of the first drive module as the first drive module moves along the longitudinal axis.

In one implementation the sterile barrier includes a second drive module moving along the longitudinal axis of the drive body independently of the first drive module; wherein the first free edge and the second free edge of the sterile barrier, adjacent the second drive module resiliently move away from the longitudinal axis and back to the longitudinal axis as the second drive module moves along the longitudinal axis.

In one implementation the sterile barrier includes a third drive module moving along the longitudinal axis of the drive body independently of the first drive module and the second drive module; wherein the first free edge and the second free edge of the sterile barrier, adjacent the third drive module resiliently move away from the longitudinal axis and back to the longitudinal axis as the third drive module moves along the longitudinal axis.

In one implementation the sterile barrier includes a first cassette operatively engaging a percutaneous device, the first cassette being releasably secured to the first drive module, wherein the sterile barrier comprises a drive module drape secured to the first cassette and removably covering a portion of the first drive module.

In one implementation the first cassette covers a first side of the first drive module and the drive module drape covers at least one additional side of the first drive module.

In one implementation the first cassette and the drive module drape covers substantially all sides of the first drive module.

In one implementation the drive module drape is a rigid member pivotally attached to the first cassette.

In one implementation the drive module drape is a flexible material secured to the first cassette.

In accordance with another embodiment, a catheter based procedure system comprises a robotic drive comprising a drive body, and a support arm. The drive body is supported by the support arm. A first drive module and a second drive module moves along a longitudinal axis of the drive body. A sterile barrier comprises a first flexible portion covering the support arm and a portion of the drive body, a second portion being more rigid than the first flexible portion and being removably connected to the drive body, and a third resilient portion extending from the second portion, the third resilient member having a first free edge proximate the longitudinal axis and being adjacent the first drive module.

In one implementation the third resilient portion includes a second free edge separate from the first free edge and proximate the longitudinal axis, the first drive module being movable between the first free edge and the second free edge.

In accordance with another embodiment, a method of applying a sterile barrier on a robotic drive having a drive body and a first drive module moving along a longitudinal axis of the drive, the method comprises providing a sterile barrier having a resilient member having a first free edge; securing the sterile barrier to the drive body; and aligning the first free edge of the resilient member along the longitudinal axis of the drive body adjacent a first drive module, the first free edge adjacent the first drive module being resiliently biased away from and returned to the longitudinal axis as the first drive module moves along the longitudinal axis about the robotic drive.

In one implementation the method further comprises securing a first cassette to an exposed portion of the first drive module, wherein the first cassette and the sterile barrier covers substantially all sides of the first drive module. The first cassette and the drive module drape covers substantially all sides of the first drive module.

In one implementation the method further comprises removably securing a rigid portion of the sterile barrier to the drive body.

BRIEF DESCRIPTION OF THE DRAWINGS

The invention will become more fully understood from the following detailed description, taken in conjunction with the accompanying drawings, wherein the reference numerals refer to like parts in which:

FIG. 3 is a right perspective view of a drape on catheter procedure system.

FIG. 4 is a left perspective view of a drape on catheter procedure system.

DETAILED DESCRIPTION OF THE EXAMPLE EMBODIMENTS

Figure 1:
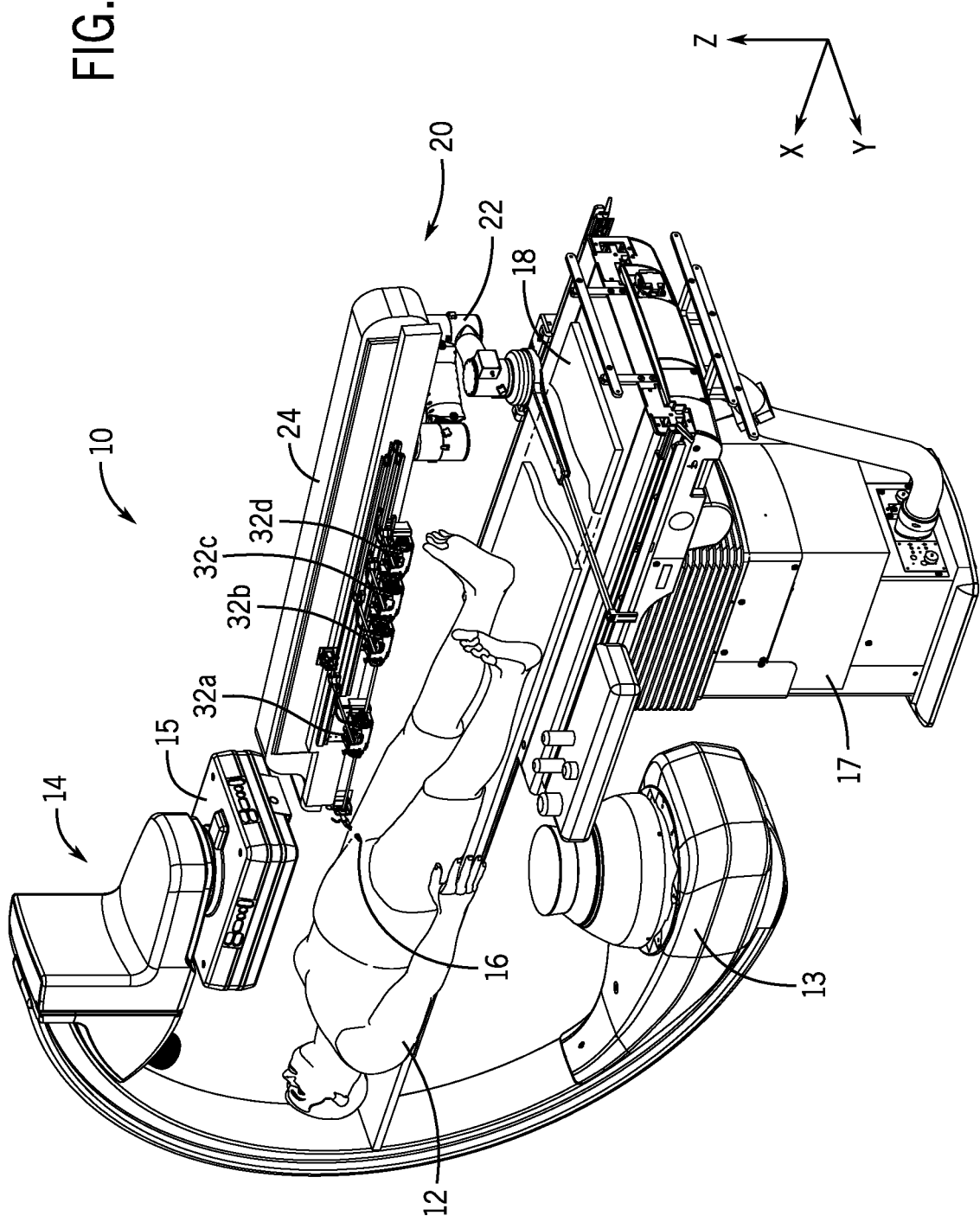
FIG. 1 is a perspective view of an exemplary catheter procedure system in accordance with an embodiment.

FIG. 1 is a perspective view of an example catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station (not shown). Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, the patient table 18 (as shown in FIG. 1), a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow a user or operator to perform a catheter-based medical procedure via a robotic system by operating various controls such as the controls and inputs located at the control station. Bedside unit 20, and in particular robotic drive 24, may include any number and/or combination of components to provide bedside unit 20 with the functionality described herein. The robotic drive 24 includes a plurality of device modules 32a-d mounted to a rail or linear member. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with the control station (not shown), allowing signals generated by the user inputs of the control station to be transmitted wirelessly or via hardwire to the bedside unit 20 to control various functions of bedside unit 20. As discussed below, control station 26 may include a control computing system 34 (shown in FIG. 2) or be coupled to the bedside unit 20 through the control computing system 34. Bedside unit 20 may also provide feedback signals (e.g., loads, speeds, operating conditions, warning signals, error codes, etc.) to the control station, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. The control station or other similar control system may be located either at a local site (e.g., local control station 38 shown in FIG. 2) or at a remote site (e.g., remote control station and computer system 42 shown in FIG. 2). Catheter procedure system 10 may be operated by a control station at the local site, a control station at a remote site, or both the local control station and the remote control station at the same time. At a local site, a user or operator and the control station are located in the same room or an adjacent room to the patient 12 and bedside unit 20. As used herein, a local site is the location of the bedside unit 20 and a patient 12 or subject (e.g., animal or cadaver) and the remote site is the location of a user or operator and a control station used to control the bedside unit 20 remotely. A control station (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

The control station generally includes one or more input modules 28 configured to receive user inputs to operate various components or systems of catheter-based procedure system 10. In the embodiment shown, control station allows the user or operator to control bedside unit 20 to perform a catheter-based medical procedure. For example, input modules 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include one or more touch screens, joysticks, scroll wheels, and/or buttons. In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance. Device selection buttons allow the user or operator to select which of the percutaneous intervention devices loaded into the robotic drive 24 are controlled by input modules 28. Automated move buttons are used to enable algorithmic movements that the catheter-based procedure system 10 may perform on a percutaneous intervention device without direct command from the user or operator 11. In one embodiment, input modules 28 may include one or more controls or icons (not shown) displayed on a touch screen (that may or may not be part of a display), that, when activated, causes operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with the control station. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure. The image or images may be displayed on display 30. For example, images may be displayed on a display to allow the user or operator to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
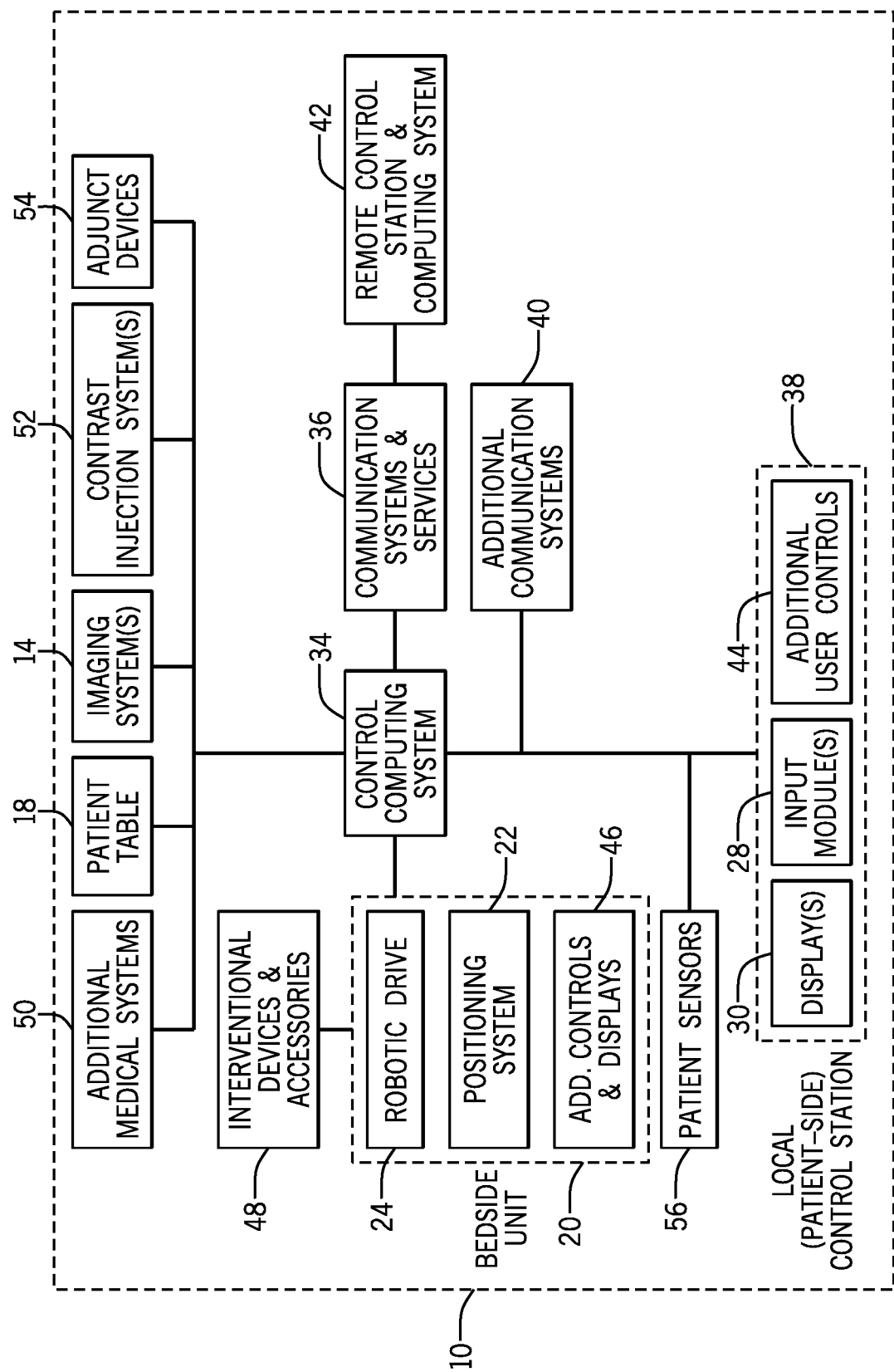
FIG. 2 is a schematic block diagram of an exemplary catheter procedure system in accordance with an embodiment.

FIG. 2 is a block diagram of catheter-based procedure system 10 in accordance with an example embodiment. Catheter-procedure system 10 may include a control computing system 34. Control computing system 34 may physically be, for example, part of a control station. Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input modules 28 (e.g., of a control station such as a local control station 38 or a remote control station 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images. In another embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

As mentioned, control computing system 34 is in communication with bedside unit 20 which includes a robotic drive 24, a positioning system 22 and may include additional controls and displays 46 and may provide control signals to the bedside unit 20 to control the operation of the motors and drive mechanisms used to drive the percutaneous intervention devices (e.g., guidewire, catheter, etc.). The various drive mechanisms may be provided as part of a robotic drive 24.

Referring to FIG. 3 robotic drive robotic drive 24 includes a drive body 100 having a top wall 102, a proximal wall 104, a distal wall 106, a first longitudinal wall 108, and a second longitudinal wall 110. When robotic drive 24 is in an in-use position on patient table 18 top wall 102 is the furthest wall from patient table 18, proximal wall 104 is the wall most proximal or closest to a foot of patient table 18. Distal wall 106 is the wall most distal or closest to the head of patient table 18. The first longitudinal wall 108 and the second longitudinal wall 110 are the walls closet to and furthest from the bed rail 112 closest the base of positioning system 22. Drive body 100 includes a bottom wall 114 that is closest to patient table 18 when robotic drive 24 is in the in-use position. Bottom wall 114 has a slot 116 extending longitudinally between proximal wall 104 and distal wall 106.

A first device module 32*a* includes a drive module 118 that is driven along a longitudinal axis 128 of drive body 100 and includes a connecting stage member 120 extending through slot 116 and is operatively engaged with a drive mechanism that moves drive module 118 along the longitudinal axis of drive body 100. Drive body 100 of robotic drive 24 and drive module 118 are capital equipment and is not part of a sterile portion of bedside unit 20.

Figure 7:
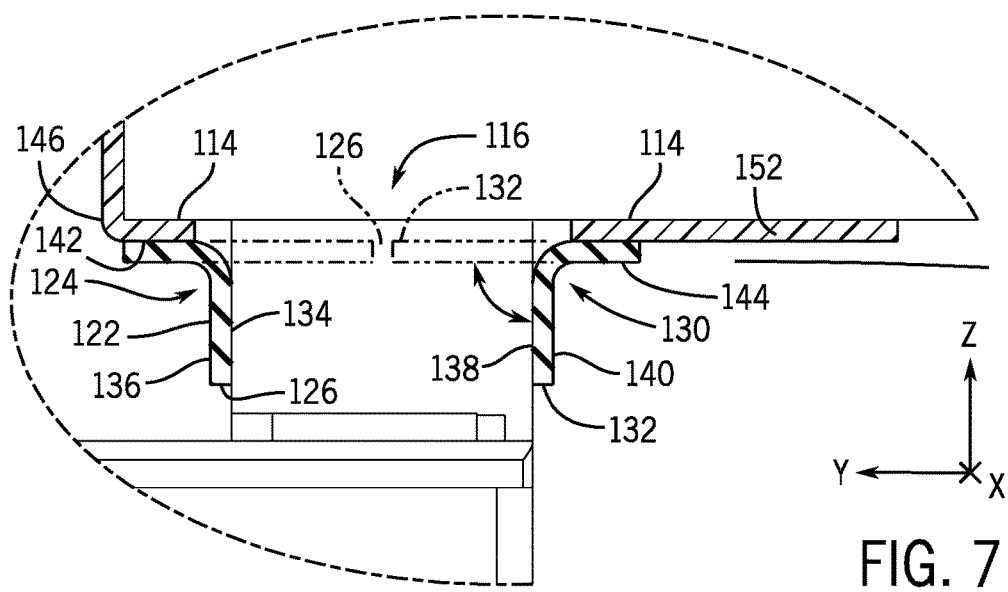
FIG. 7 is a close up view of the drape on the catheter procedure system of FIG. 6 taken generally along line 7-7.
Figure 8:
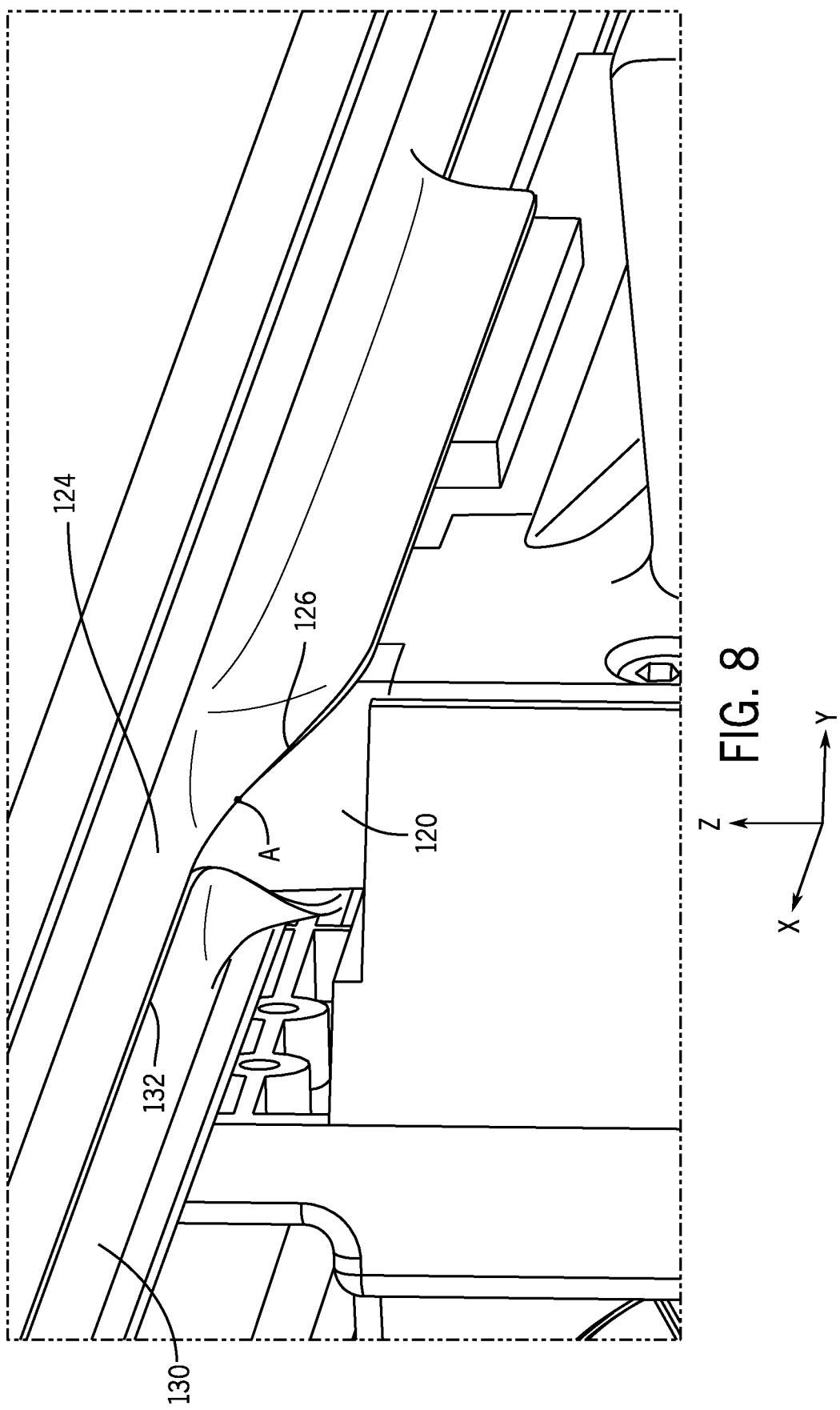
FIG. 8 is a close-up view of the resilient drape portion and a drive module.

Referring to FIG. 7 and FIG. 8 a sterile barrier 122 includes a first resilient member 124 having a first free edge 126 proximate longitudinal axis 128. Longitudinal axis 128 is the axis along which the drive modules move. Sterile barrier 122 provides a sterile barrier between the bottom wall 114 and slot 116 of drive body 100. A portion of first free edge 126 adjacent the first drive module 32*a* is resiliently biased away from and returned to the longitudinal axis as the first drive module 32*a* moves along the longitudinal axis. First resilient member 124 extends from a proximal end of slot 116 to a distal end of slot 116 such that the substantially the entire slot 116 is covered. Only a portion of first free edge 126 of first resilient member 124 that is closely adjacent first drive module 32*a* is biased away from the longitudinal axis. Stated another way the portion of first free edge 126 of first resilient member 124 that is distal first drive module 32*a* is not biased away from the longitudinal axis. By way of example and referring to FIG. 8 a region of first free edge 126 proximate point A that is closely adjacent first drive module 32*a* is biased away from the longitudinal axis 128. Once first drive module 32*a* moves along the longitudinal axis 128 such that region of first free edge 126 proximate point A is no longer closely adjacent first drive module 32*a* the region of first free edge 126 proximate point A will resiliently return to the longitudinal axis. In one implementation the free edges of first resilient member 124 and second resilient member 130 are moved from and return to the longitudinal axis or non-stressed position between within 0.75 cm of contacting drive module drape 158. In one implementation the free edges of first resilient member 124 and second resilient member 130 move from and return to their non-stressed position in less than 1.0 cm. In one implementation the free edges of first resilient member 124 and second resilient member 130 move from and return to their non-stressed position in less than 0.5 cm.

In one implementation robotic drive 24 includes a second device module 32b including a separate drive module and a separate stage extending through slot 116. Second device module 32b is translated along the longitudinal axis of the drive body independently of first drive module 32a. Where there are two separate drive modules a second portion of first resilient member 124 closely proximate second device module 32b is biased away from the longitudinal axis. In the implementation of two independently moving drive modules a first portion and a second portion proximate first drive module 32a and second device module 32b respectively are biased away from the longitudinal axis, while the remaining portion of first resilient member 124 not closely adjacent to first drive module 32a and second device module 32b are not biased away from the drive body longitudinal axis. Similarly, where there are more than two drive modules only the portions of first resilient member 124 closely adjacent each drive module will be biased away from the drive body longitudinal axis. Each portion of first resilient member 124 that is biased away from the drive body longitudinal axis returns to a non-stressed condition such that first free edge 126 of such portion returns to a position proximate the drive body longitudinal axis. In this manner slot 116 between drive modules is substantially covered by first resilient member 124. Stated another way in one implementation a third drive module moves along the longitudinal axis of the drive body independently of the first drive module and the second drive module. A portion of first free edge 126 and a portion of second free edge 132 adjacent the third drive module resiliently move away from the longitudinal axis and back to the longitudinal axis as the third drive module moves along the longitudinal axis.

Figure 6:
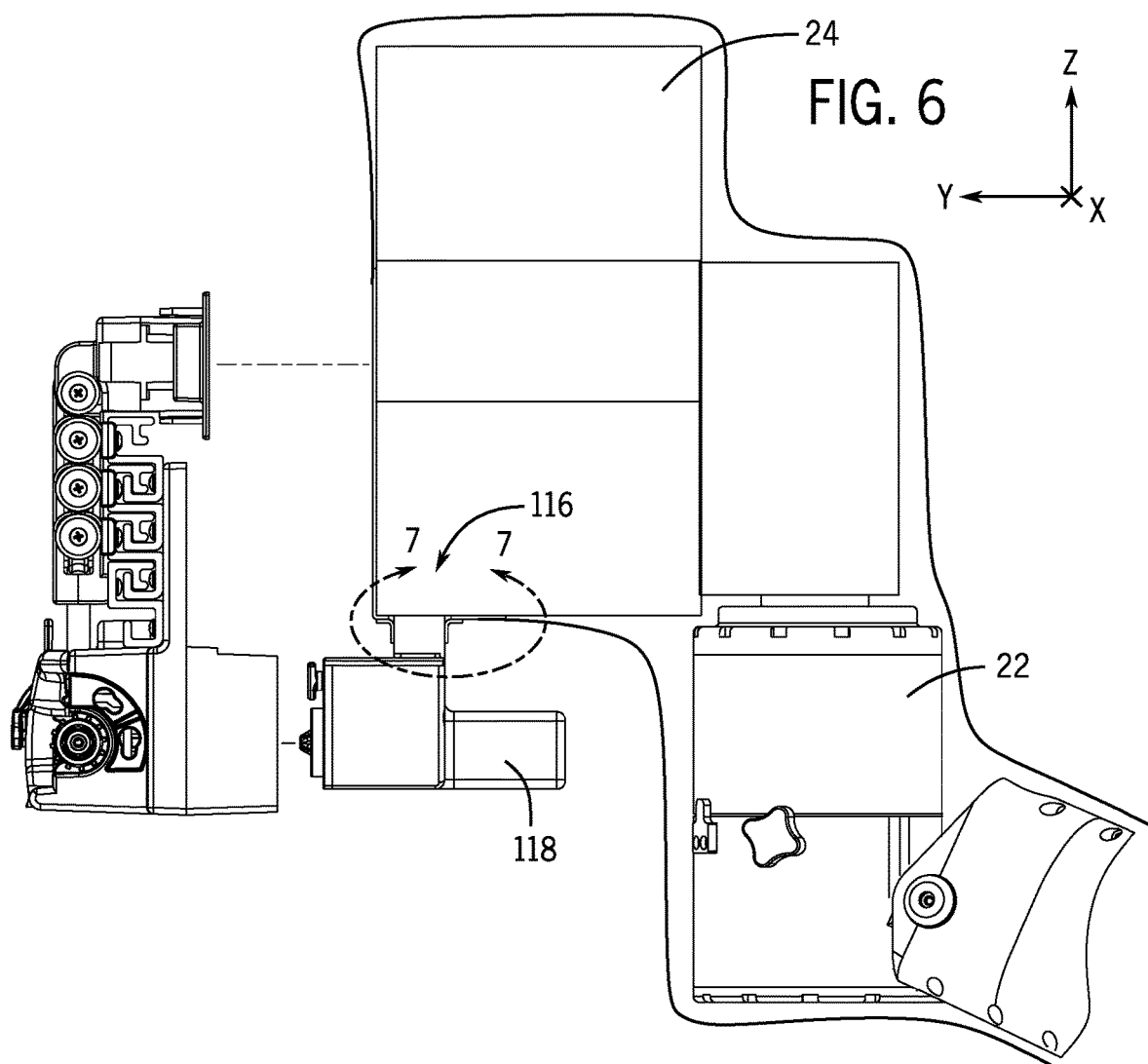
FIG. 6 is an end view of the drape on the catheter procedure system

Referring to FIG. 6 and FIG. 7 in one implementation sterile barrier 122 includes a second resilient member 130 having a second free edge 132 that is proximate first resilient member 124. In one implementation first resilient member 124 and second free edge 132 overlap. In one implementation first resilient member 124 and second free edge 132 closely abut. In one implementation first resilient member 124 and second free edge 132 are spaced from one another a predetermined distance. First resilient member 124 extends from a first edge of slot 116 and second resilient member 130 extends from a second edge of slot 116. Second resilient member 130 is formed of a resilient material such that second free edge 132 closely adjacent a drive module is biased away from the longitudinal axis. In one implementation first resilient member 124 and second resilient member 130 are the same material. In one implementation first resilient member 124 and second resilient member 130 are a different material.

Referring to FIG. 7 first resilient member 124 includes a first side 134 and an opposing second side 136. First side 134 faces bottom wall 114 and slot 116 and second side 136 faces away from the bottom wall 114 and slot 116. The region of first side 134 of first resilient member 124 that is closely adjacent a device module is biased away from bottom wall 114 and slot 116 and returns toward bottom wall 114 and slot 116 once a device module is no longer closely adjacent. A portion of first side 134 contacts an outer surface of the first drive module as the first drive module moves along the longitudinal axis. In this manner second side 134 remains part of the sterile environment while first side 134 contacts the non-sterile environment of robotic drive 24.

Similarly, second resilient member 130 includes a first side 138 and a second side 140. First side 138 faces bottom wall 114 and slot 116 and second side 140 faces away from the bottom wall 114 and slot 116. The region of second resilient member 130 that is closely adjacent a device module is biased away from bottom wall 114 and slot 116 and returns toward bottom wall 114 and slot 116 once a device module is no longer closely adjacent. In this manner second side 140 remains part of the sterile environment while first side 138 contacts the non-sterile environment of robotic drive 24.

The stage portion of each drive module extends between first free edge 126 of first resilient member 124 and second free edge 132 of second resilient member 130. In one implementation the region of first side 134 of first resilient member 124 and the region of first side 138 of second resilient member immediately adjacent each drive module contacts a portion of that drive module.

Referring to FIG. 7, a longitudinal portion 142 of first resilient member 124 distal first free edge 126 is secured to drive body 100 and a longitudinal portion 144 of second resilient member 130 distal free edge 132 is secured to drive body 100. In one implementation a first rigid member 146 is releasably secured to drive body 100 and first resilient member 124 is secured to first rigid member 146. First resilient member 124 is secured to drive body 100 via first rigid member 146. In one embodiment first rigid member 146 is adjacent to first longitudinal wall 108 along a first wall portion 148 (FIG. 5) of first rigid member 146 in a secured position. First rigid member 146 includes a second wall portion 150 (FIG. 5) extending away from first wall portion 148 and positioned adjacent bottom wall 114. In one implementation first wall portion 148 is secured to drive body 100 on first longitudinal wall 108. In one implementation second wall portion 150 is secured to bottom wall 114.

A second rigid member 152 (FIG. 5) is secured to bottom wall 114 adjacent the second side of slot 116. Second rigid member 152 is removably secured to bottom wall 114 of drive body 100. Second resilient member 130 is secured to a longitudinal portion of second rigid member 152.

First rigid member 146 and second rigid member 152 are coupled to drive body 100 with a coupler such as a fastener, magnet, hook and loop, or other know couplers. Since first resilient member is secured to the first rigid member and the second resilient member is secured to the second rigid member, the first resilient members are removably coupled to drive body 100.

In one implementation a first cassette 154 (FIG. 9) operatively engaging a percutaneous device, is releasably secured to first drive module 32a. Cassette 154 is secured to first drive module 32a such that first wall portion 148 of first rigid member 146 (FIG. 5) is between drive body 100 and first cassette 154. Cassette 154 is part of the sterile environment and separated from drive body 100 by sterile barrier 122.

Figure 5:
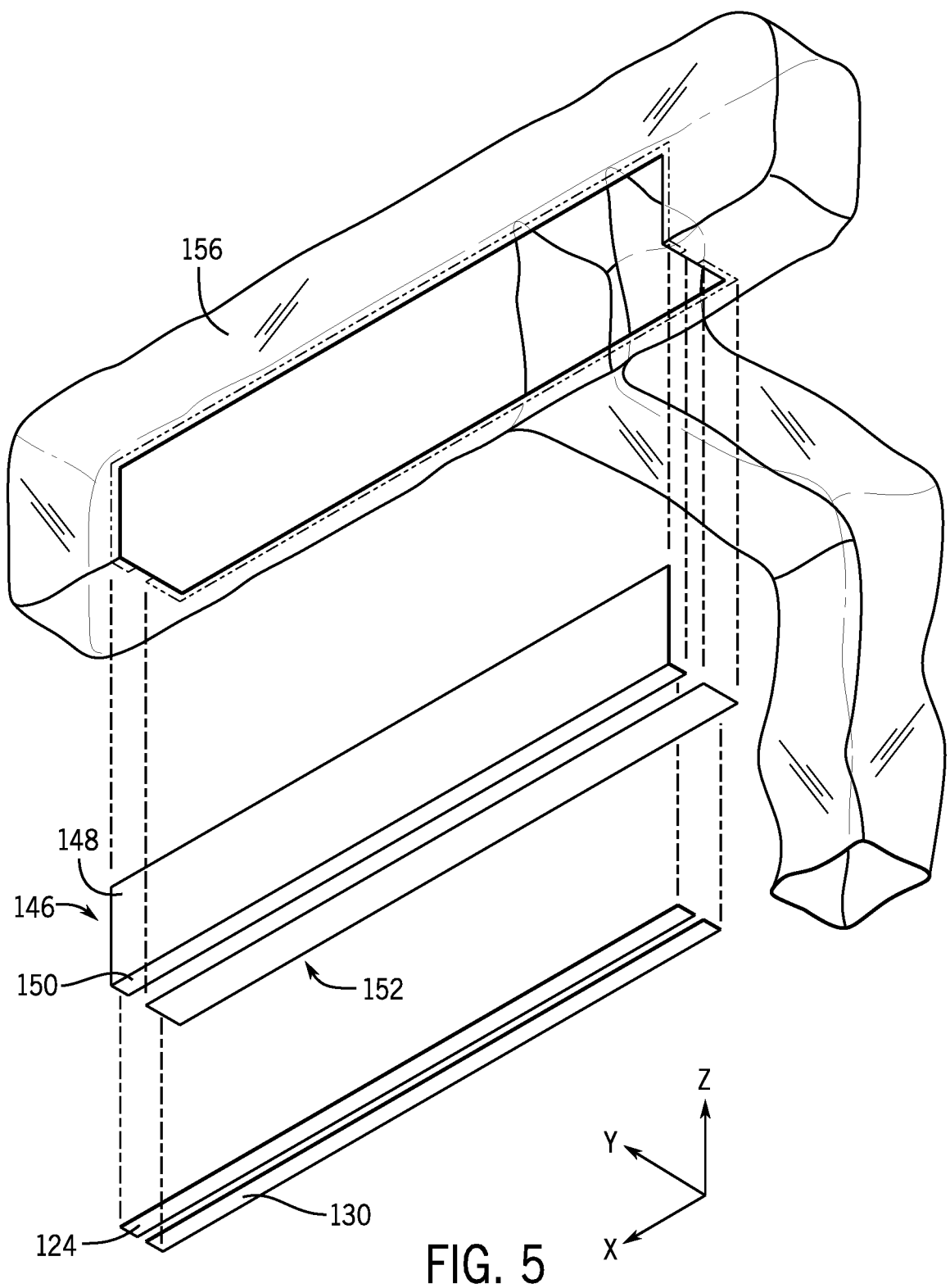
FIG. 5 is an exploded view of a drape assembly

Referring to FIG. 3, FIG. 4 and FIG. 5 sterile barrier 122 includes a flexible drape portion 156 covering portions of robotic drive 24 and positioning system 22. Flexible drape covers top wall 102, proximal wall 104, distal wall 106, second longitudinal wall 110 and at least a portion of first longitudinal wall 108. In one implementation first rigid member 146 also covers a portion of bottom wall 114. In one implementation first rigid member 146 is secured to flexible drape portion 156 such that the entire first longitudinal wall 108 is covered by sterile barrier 122. In one implementation second rigid member 152 is secured to flexible drape portion 156 covering at least part of bottom wall 114. In one implementation flexible drape portion 156 is formed from a polyethylene material having a thickness of 0.002 inches (0.00508 cm) or other materials known in the art can be used. First rigid member 146 is formed from a polycarbonate material having a thickness of 0.03 inches (0.0762 cm) or other materials known in the art can be used. First resilient member 124 and second resilient member 130 are formed of EPDM (Ethylene Propylene Diene Monomer) rubber having a thickness of 1/32 inch (0.0794 cm). First rigid member 146 has a rigidity greater than flexible drape portion 156. First resilient member 124 and second resilient member 130 are more resilient than flexible drape portion 156. In one implementation first wall portion 148 is secured to flexible drape portion 156 forming a continuous sterile barrier. First wall portion 148 is secured to flexible drape portion 156 with an adhesive bond, sonic welding, mechanical fastener, tape or other connections known in the art. Second rigid member 152 is similarly fastened to a portion of flexible drape portion 156 in a similar manner. First resilient member 124 and second side 140 are secured to first rigid member first rigid member 146 and second rigid member 152 respectively in a similar manner. Second rigid member 152 may also be connected to a portion of flexible drape portion 156 in a similar manner. Flexible drape portion 156 may have a slit or free edges to allow for easy installation onto robotic drive 24 and positioning system 22 and the slit may be covered by an adhesive tape or other mechanical fastener known in the art.

Figure 9:
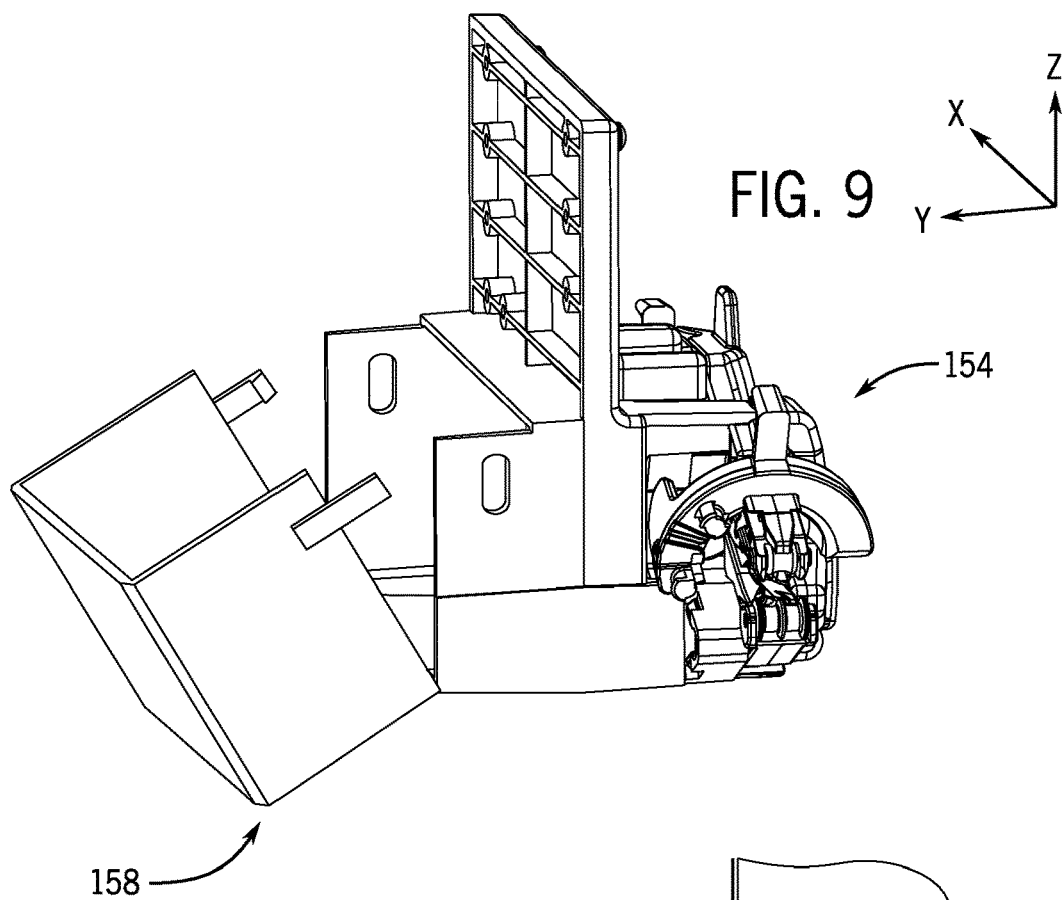
FIG. 9 is a perspective view of a cassette with a rigid drape portion.
Figure 10:
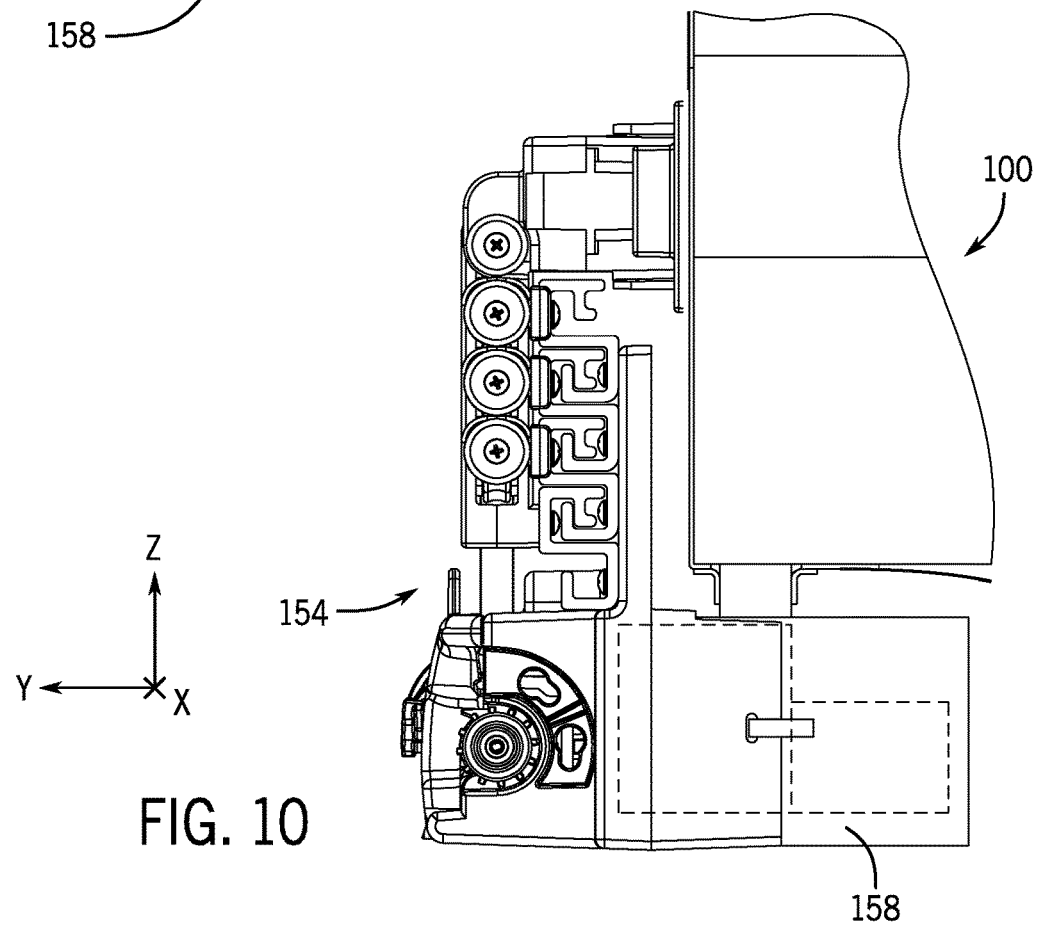
FIG. 10 is an end view of the cassette with rigid drape portion on the catheter procedure system.

Referring to FIG. 9 and FIG. 10 a drive module drape 158 is secured to cassette 154. In one implementation drive module drape 158 is pivotally secured to cassette 154 to releasably cover a portion of drive module 118. Drive module drape 158 moves from an uncovered position to a covered position. Drive module drape 158 includes a bottom wall, a first side wall, a second side wall, and a third rear wall. In a covered position drive module drape 158 covers at least a portion of at least one of a bottom wall, a first side wall, a second side wall, and third rear wall of drive module 118. In one implementation cassette 154 is releasably secured to at least one side of the drive module 118. In one implementation substantially all of the drive module 118 is covered by drive module drape 158 and cassette 154. In one implementation drive module drape is rigid and includes a fastener to fasten drive module drape 158 to cassette 154.

Figure 11A:
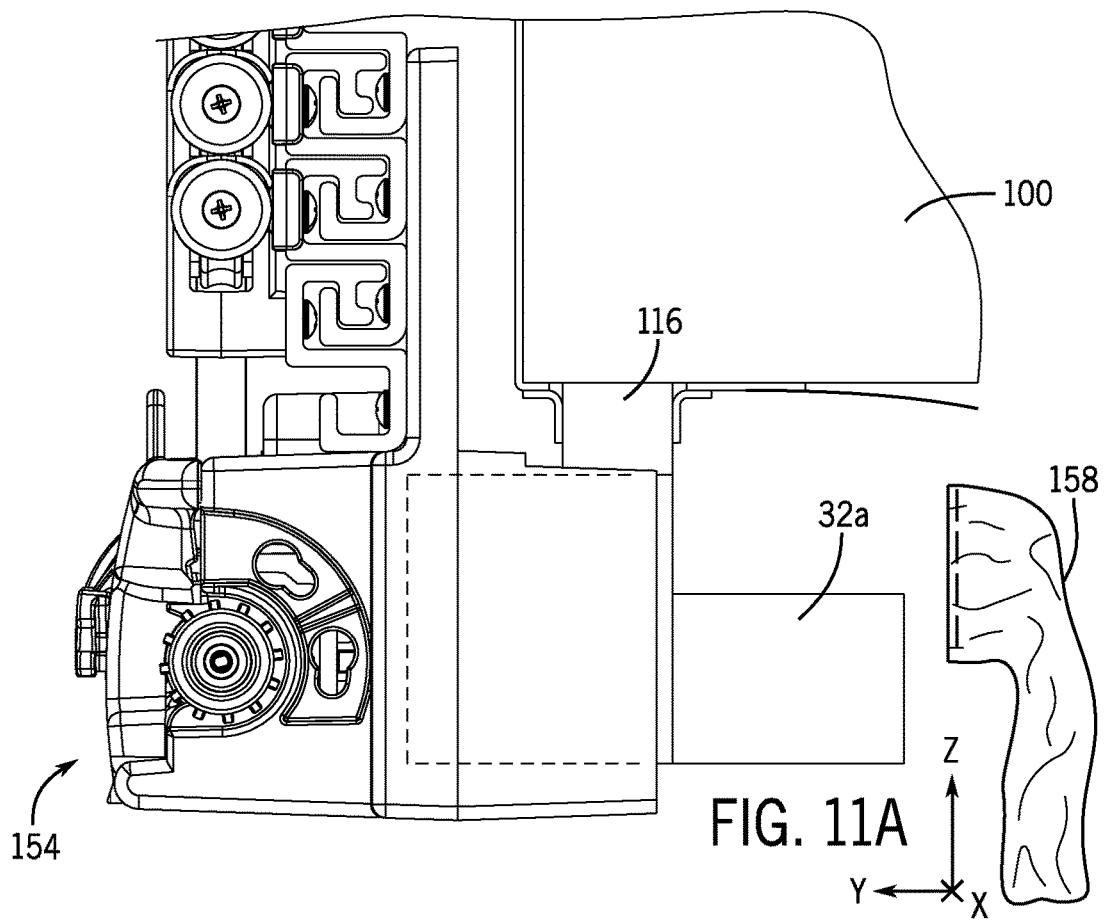
FIG. 11A is an exploded view of a cassette attached to a drive module and a flexible drape.
Figure 11B:
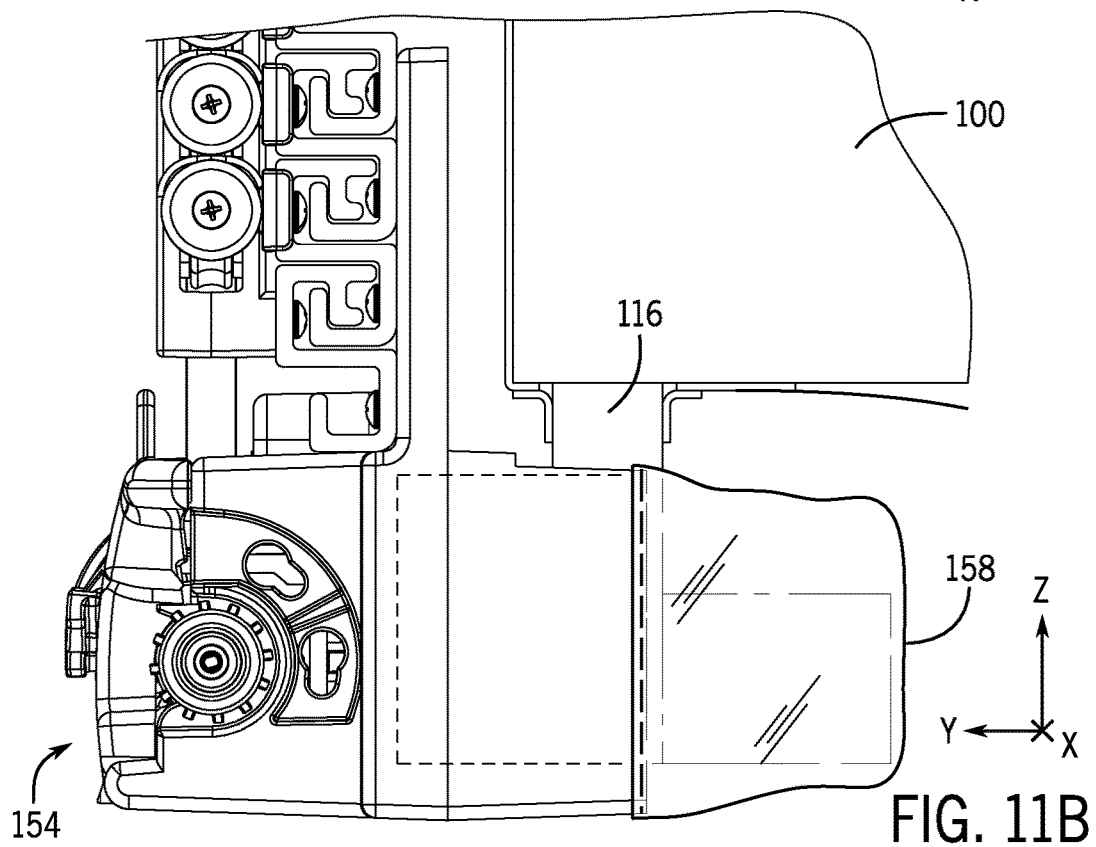
FIG. 11B is an end view of the cassette with flexible drape portion on the catheter procedure system

Referring to FIG. 11A and FIG. 11B drive module drape 158 is a flexible member having a bag shape with an opening, side wall and bottom that is removably placed over drive module 118 to substantially cover exposed portions of drive module 118. In one implementation flexible drive module drape 158 is also attached to a portion of cassette 154.

In one implementation sterile barrier 122 covers a robotic drive including a support arm of positioning system 22, a drive body 100 supported by the support arm. A first drive module 32a and a second drive module 32b move along a longitudinal axis of the drive body 100. Sterile barrier 122 includes a first flexible portion 156 covering the robotic arm and a portion of the drive body 100, a second rigid member 146 being more rigid than the first flexible portion 156. The second rigid portion 146 being removably connected to drive body 100. Sterile barrier 122 also includes a resilient member 130 extending from the second rigid member 152, the resilient member 130 having a first free edge 132 proximate a longitudinal axis of the drive body and being adjacent the first drive 32a. In one implementation the resilient member 130 includes a free edge 132 separate from the first free edge 126 and proximate the longitudinal axis, the drive module 32a being movable between the first free edge and the second free edge.

Referring to FIG. 9, FIG. 10, FIG. 11A and FIG. 11B in one implementation bedside unit 20 has a robotic drive 24 with a first drive module moving along a longitudinal axis of a drive body. A first cassette is removably connected to the first drive module. A drive module drape is attached to the first cassette and removably covers a portion of the first drive module. In one implementation drive module drape is formed of a rigid material operatively secured to the cassette. In one implementation drive module drape is formed of a flexible material that is operatively secured to the cassette.

Figure 12:
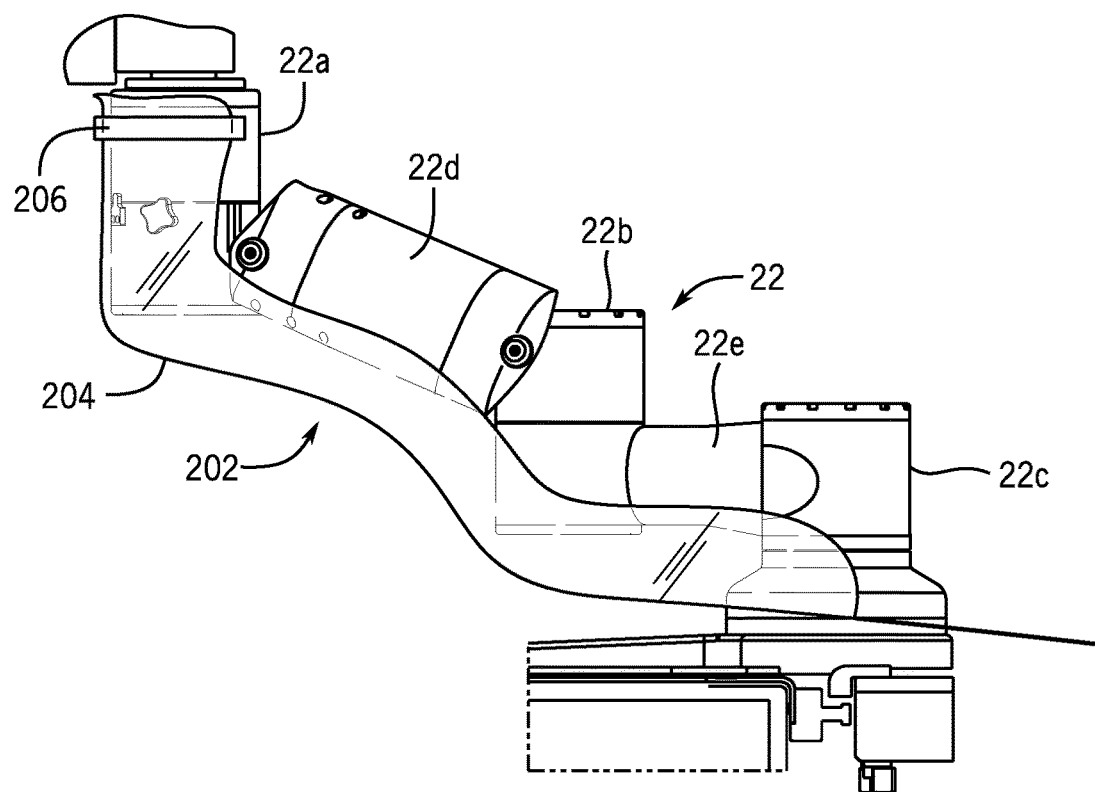
FIG. 12 is a side view of a first arm drape covering a portion of the robotic arm.

Referring to FIG. 12 in one implementation a sterile barrier system 200 includes a bottom arm sterile barrier 202 that covers the bottom portion of positional system 22. Bottom arm sterile barrier 202 may also be used in conjunction with sterile barrier 122 discussed herein.

Figure 13:
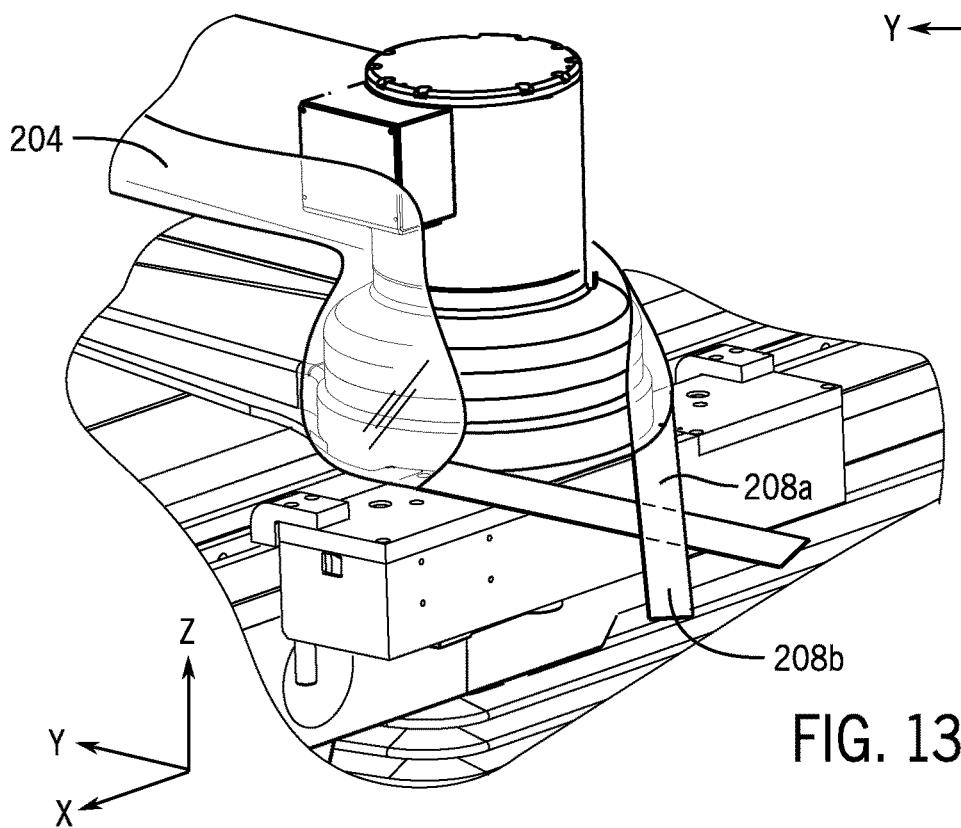
FIG. 13 is a partial; perspective view of the first arm drape and robotic arm of FIG. 12.

Bottom arm sterile barrier 202 includes a flexible drape portion 204 coupled to a clip 206 that is removably coupled to positioning system 22 about an upper rotational joint 22a. Bottom arm sterile barrier 202 extends from clip 206 below the positioning system 22 from upper rotational joint 22a to the bottom rotational joint 22c. Referring to FIG. 13 a pair of straps 208a and 208b extending from a terminal end of flexible drape portion 204 is secured to a base portion positioning system 22. In this manner flexible drape portion 204 covers the bottom portion of positioning system 22. In one implementation bottom arm sterile barrier 202 includes a pocket (not shown) secured to flexible drape portion 204 adjacent clip 206 to allow a user to position clip 206 onto positioning system 22 without a user touching a sterile portion of flexible drape portion 204.

Figure 14:
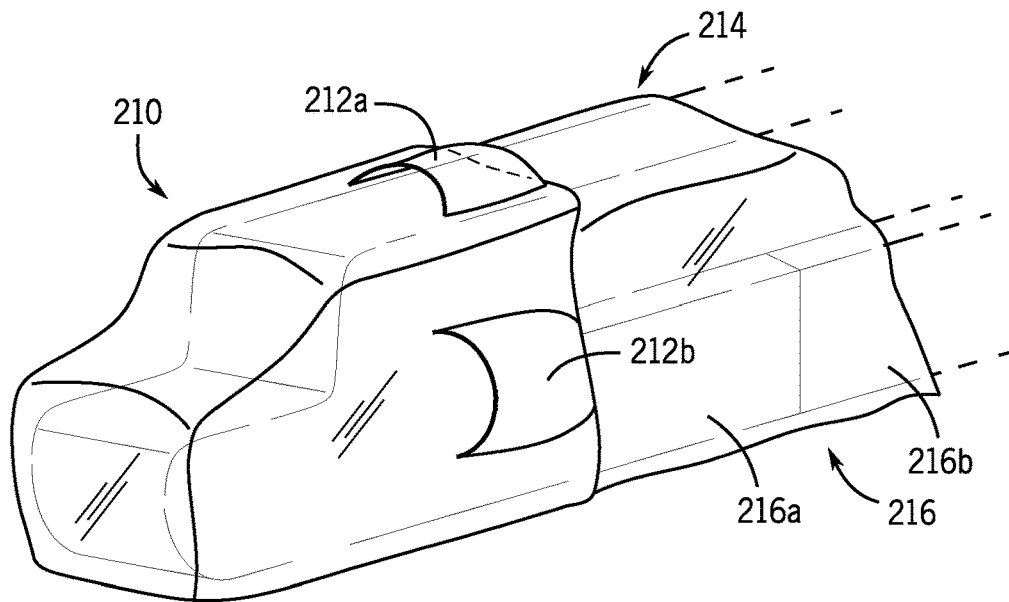
FIG. 14 is a partial perspective view of a sterile barrier system.

Referring to FIG. 14 sterile barrier system 200 includes a distal drape portion 210 defining an interior cavity that is pulled over the distal end of robotic drive 24. Distal drape portion 210 includes a first pocket 212a on the external portion of distal drape portion 210 that allows a user to place the user's hand within the first pocket 212a to pull the distal drape portion 210 over the distal end of robotic drive 24. In one implementation a second pocket 212b on distal drape portion 210 allow a user to place the user's second hand into second pocket 212b to assist in distal drape portion 210 over the distal end robotic drive 24. In one implementation distal drape portion 210 extends a predetermined distance from the distal end of robotic drive 24 toward the proximal end of robotic drive 24 where the predetermined distance does not extend the entire length of robotic drive 24 along the robotic drive longitudinal axis.

In one implementation a first portion of a snap (not shown) is snapped onto a second portion of a snap on the top wall 102 of robotic drive 24. Other attachment features are contemplated such as a magnet on top wall 102 of robotic drive 24 that releasably secures a magnetophilic material (such as an iron disc or washer) secured to distal drape portion 210.

In one implementation sterile barrier system 200 includes a second flexible drape portion 214 that covers a portion of first longitudinal wall 108, top wall 102 and second longitudinal wall 110. A distal portion of second flexible drape portion 214 is secured to distal drape portion 210. Sterile barrier system 200 includes a first rigid member system 216 that is similar to first rigid member 146 of sterile barrier 122. In one implementation first rigid member system 216 has a number of adjacent sections 216a, 216b, 216c, and 216d that allow each of the sections to be folded on one another for convenient packaging shipping and deployment. While rigid member system 216 is shown in one implementation having four sections it is contemplated that rigid member system 216 may include one or more sections. In one implementation the number of folds is two. In one implementation the number of folds is three. In one implementation the number of folds is between and including 2 through 4. In one implementation the number of folds is greater than 4. Each section of rigid member system 216 is connected to an adjacent section by a living hinge, where the term living hinge is a is a thin flexible hinge made from the same material as the two rigid pieces it connects. In one implementation each section is not directly connected at their proximal and/or distal ends and in one implementation each adjacent section is connected by a flexible material allowing the sections to fold against one another as an accordion. Each section of the rigid member system 216 has an upper longitudinal edge and a lower longitudinal edge.

Rigid member system 216 is unfolded and secured to a proximal end of robotic drive 24. In one implementation proximal end of the rigid member system 216 includes a proximal portion that includes a proximal cavity that is positioned over and cover a proximal end of robotic drive 24. In one implementation rigid member system 216 in one implementation is secured to a front portion of robotic drive 24 with a snap feature (or other attachment mechanisms discussed above and known in the art) where one portion of the snap is secured to the rigid member system 216 and the second snap feature is secured to the front of robotic drive 24. In one implementation (FIG. 19) each folded section of rigid member system 216 is secured to first longitudinal wall 108 of robotic drive 24. Each folded section of rigid member system 216 may be secured with a snap connection as discussed herein with a first portion of each snap connection being secured to the robotic drive and a second portion of each snap connection being secured to each folded section. In one implementation each folded portion of rigid member system 216 is secured to first longitudinal wall 108 of robotic drive 24 with a magnetic connection where one of the robotic drive 24 and rigid member system 216 includes a magnet and the other of the robotic drive 24 and rigid member system 216 includes a metal disc or member that is magnetically connected to a corresponding magnet.

Figure 19:
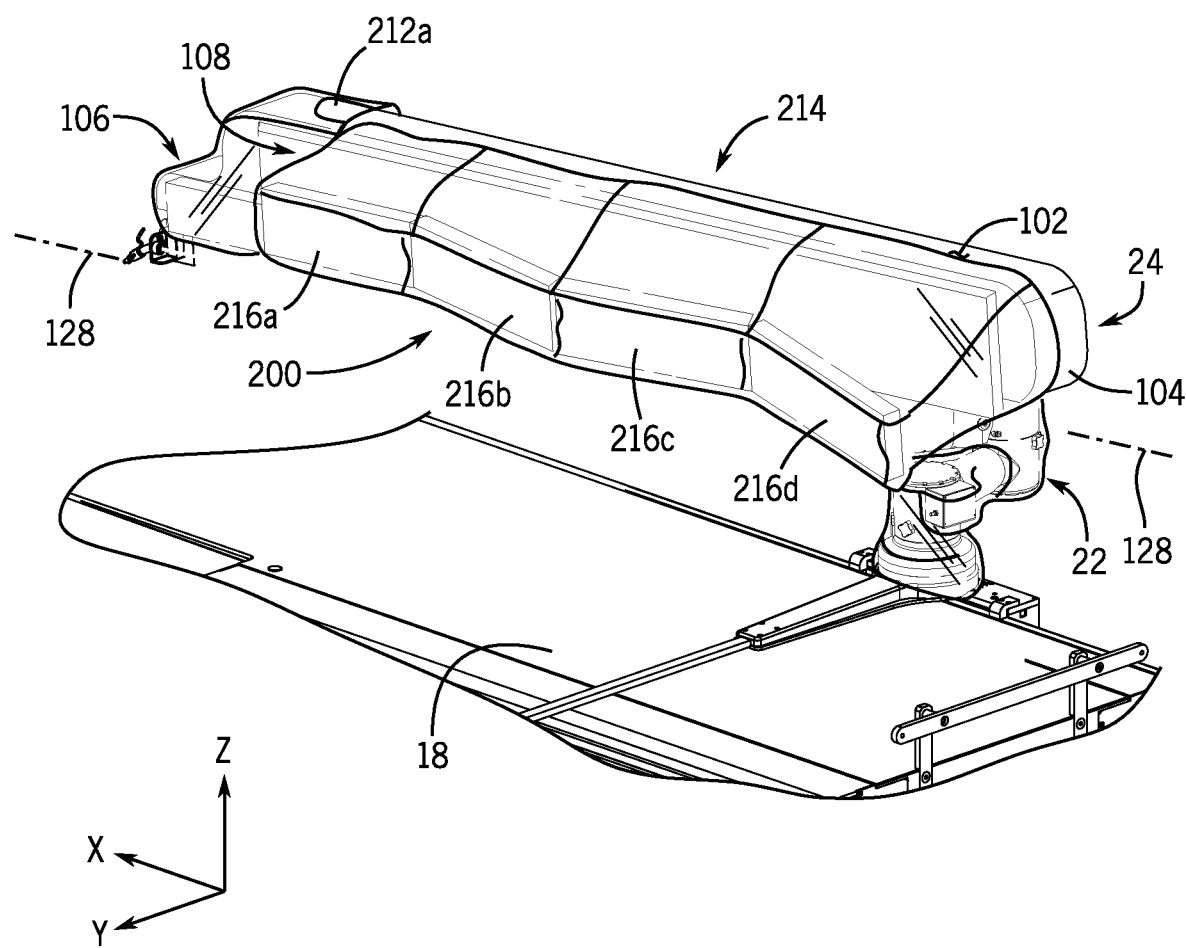
FIG. 19 is a perspective view of a sterile barrier system in the partially employed position.

A portion of second flexible drape portion 214 is secured to rigid member system 216 and is in a folded orientation when packaged. Referring to FIG. 19, the sections of rigid member system 216 are unfolded and secured to robotic drive 24 second flexible drape portion 214 is then positioned by a user upwardly covering first longitudinal wall 108, across top wall 102 and downwardly along second longitudinal wall 110. However, it is also contemplated that second flexible drape portion 214 will cover first longitudinal wall 108, top wall 102 and second longitudinal wall 110 prior to securing rigid member system 216 to robotic drive 24.

Figure 15:
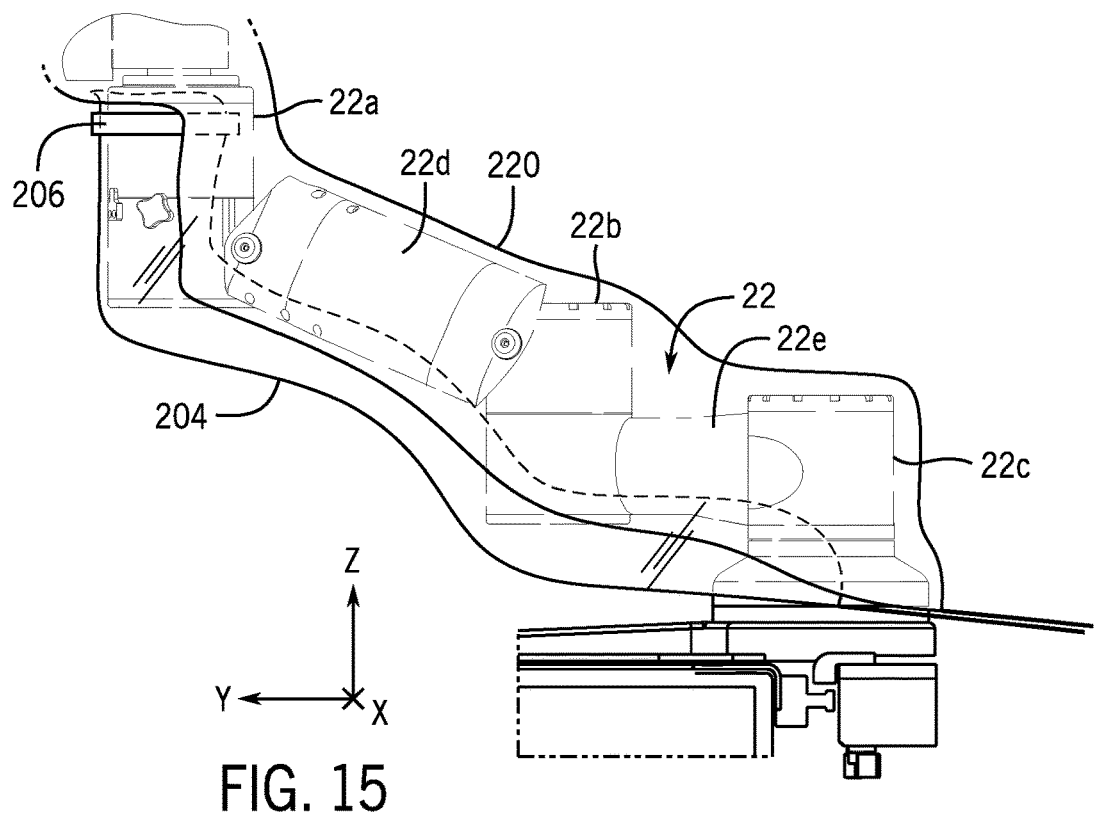
FIG. 15 is a side view of the robotic arm with the first arm drape and a second arm drape covering the robotic arm.
Figure 16:
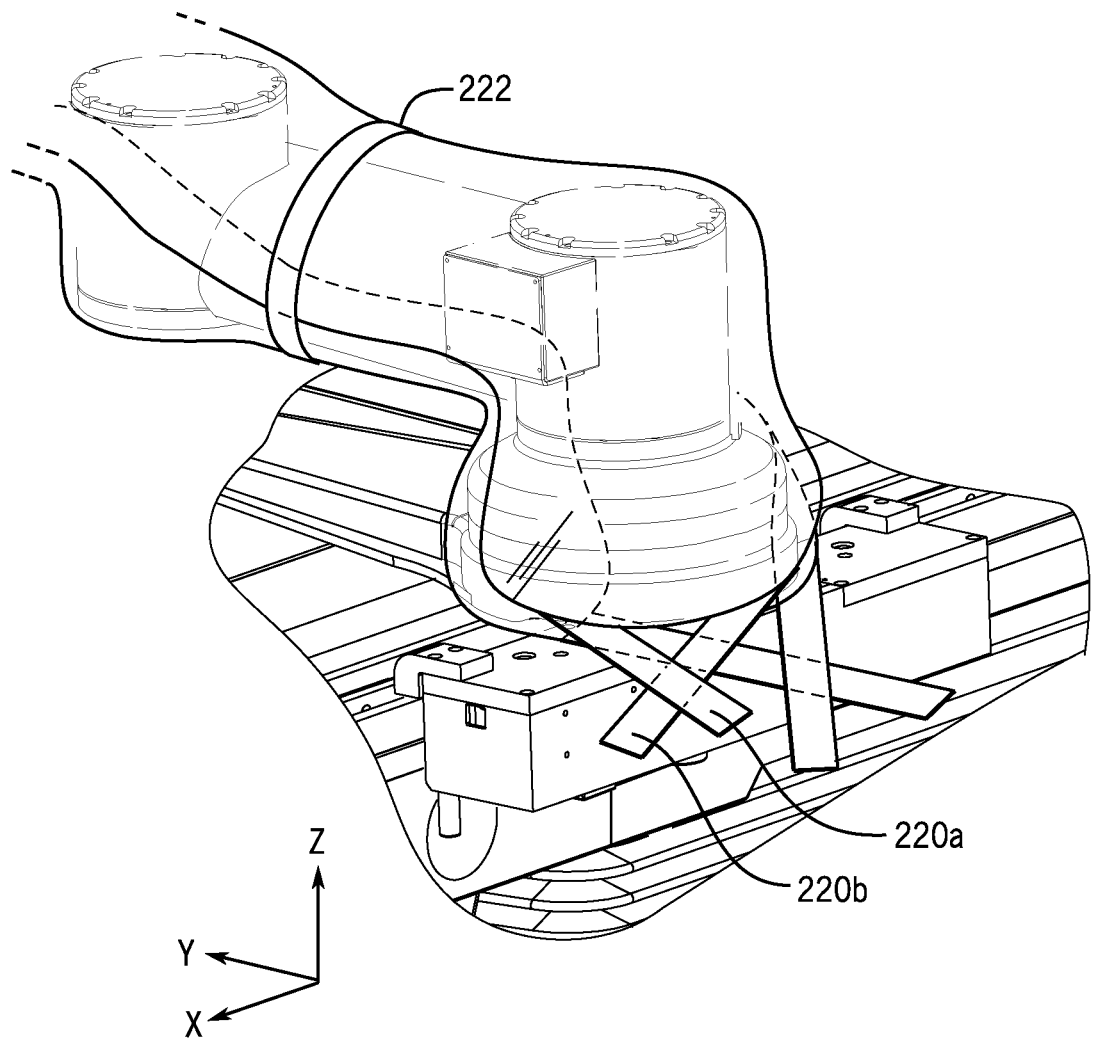
FIG. 16 is a partial perspective view of the first arm drape and second arm drape secured to the robotic arm.

An upper arm drape portion 218 extends from second flexible drape portion 214. Referring to FIG. 15 and FIG. 16, portion 218 is placed over the top positioning system 22 A free end of portion 218 is secured to the base portion of positioning system with a pair of straps 220*a* and 220*b*. Portion 218 includes a first edge and a second edge that extend over the longitudinal edges of bottom arm sterile barrier 202. A strap member 222 secures bottom arm sterile barrier 202 and portion 218 over positioning system 22 with sufficient space between to allow movement of the rotational joints 22*a*, 22*b* and 22*c* as well as arms 22*e* and 22*d* extending between the rotational joints.

Figure 17:
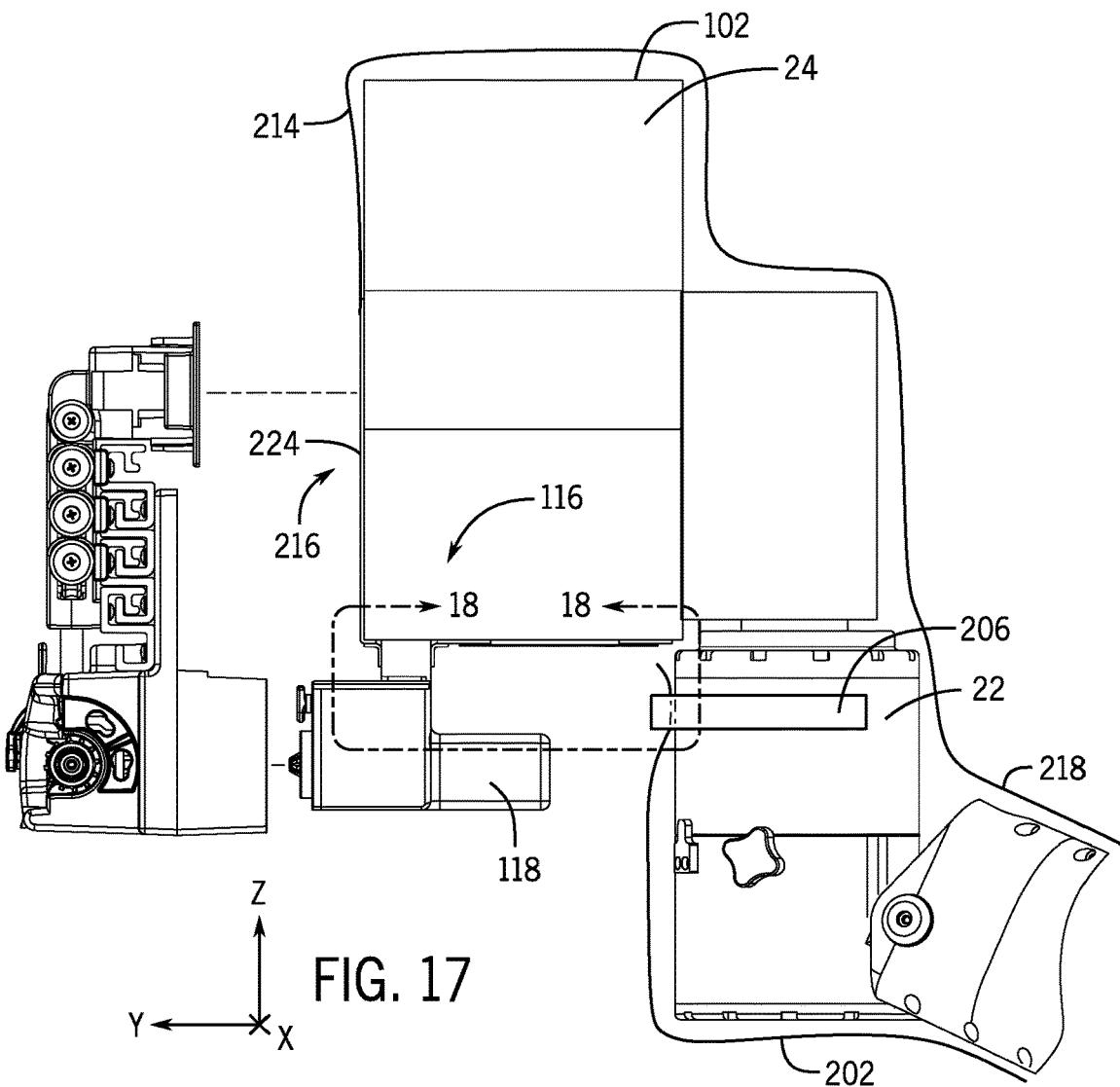
FIG. 17 is a view of the robotic drive, cassette, first arm drape, robotic drive drape and second arm drape.
Figure 18:
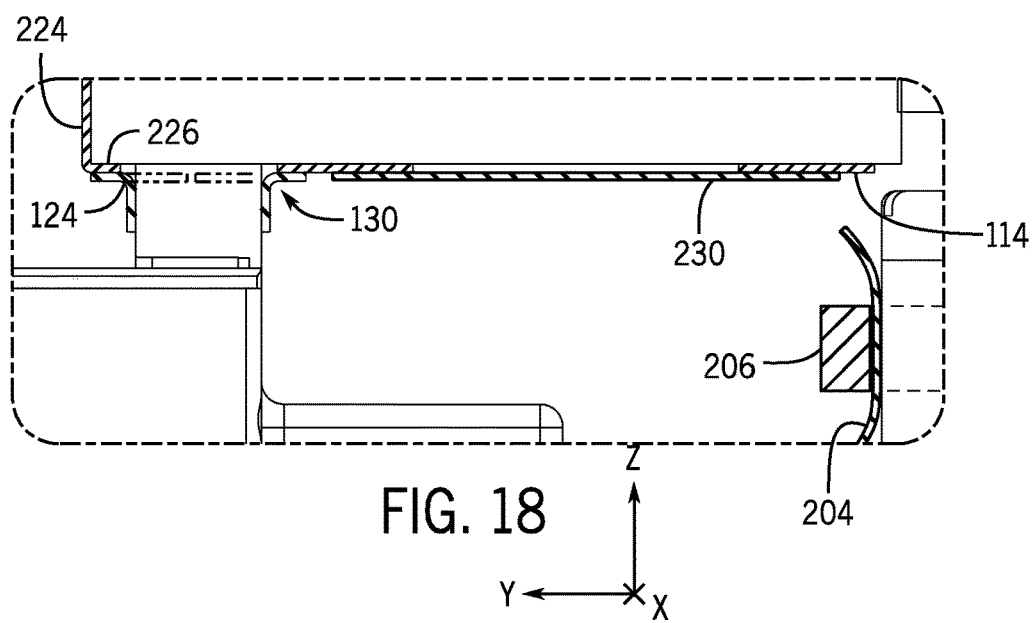
FIG. 18 is a close-up view taken generally along line 18-18 of FIG. 17.

Referring to, FIG. 5, FIG. 17 and FIG. 18 each section of rigid member system 216 has an L shape having a front panel 224 adjacent to first longitudinal wall 108 of robotic drive 24 and a second shorter portion 226 adjacent to bottom wall 114 or robotic drive 24. Note the L shape of the rigid member system 216 is similar to rigid member 146 (See FIG. 5). A first resilient member 124 second shorter portion 226 of rigid member system 216 and operates in the same manner as first resilient member 124 described above with respect to sterile barrier 122. A second rigid member 230 is secured to bottom wall 114. A second resilient member 130 is secured to second rigid member 230 and operates in the same manner as second resilient member 130 described above with respect to sterile barrier 122. In one implementation second rigid member 230 is not connected to a flexible drape portion of sterile barrier system 200. As discussed herein the sections of rigid member system 216 might have a living hinge or a flexible material connecting adjacent sections, however, in one implementation first member 130 is continuous and does not have a living hinge but is sufficiently pliable to allow second resilient member 130 to bend to allow second resilient member 130 to be packaged with the folded sections of rigid member system 216. In one implementation second resilient member 130 does have a living hinge or flexible material corresponding with the living hinge or flexible material of rigid member system 216.

In operation sterile barrier system 200 is packaged prior to use in a folded orientation and positioned in a pouch. In one implementation sterile barrier system 200 includes a bottom arm sterile barrier 202 covering a bottom of the positioning system 22 and a second drape that covers the robotic drive 24 and the top portion of the positioning system 22. In one implementation bottom arm sterile barrier 202 and the second drape are combined and packaged together.

A user takes bottom arm sterile barrier 202 and places a hand within a pocket formed in a portion of bottom arm sterile barrier 202. The user then attaches a flexible portion of bottom arm sterile barrier 202 to a portion of the positioning system with a clip while maintain the user's hand within the pocket. Straps extending from the flexible portion of bottom arm sterile barrier 202 are placed on a patient table the user then wraps the straps about a base portion of the positioning system and secures the straps to one another using a fastener such as a hook and loop style fastener (e.g., Velcro) thereby securing the bottom arm sterile barrier 202 to positioning system.

The user than grasping the folded rigid plate sections 216*a*-216*d* and inserts the user's hand into a first pocket 212*a*. The user then spreads the user's hands apart to place a distal drape portion 210 over the distal portion of the robotic drive 24. A snap located adjacent first pocket 212*a* is then attached to a corresponding snap portion on the robotic drive housing to secure the distal drape portion 210 to the robotic drive.

The user then unfolds the folded rigid plate sections one at a time making sure they are flush against the first longitudinal wall 108 of the robotic drive housing (the wall facing the user). The user then using a right index finger and middle finger presses a snap feature on a pocket adjacent the most proximal rigid plate section with a corresponding mating snap feature on the robotic drive to secure the drape plates to the robotic drive. A user places each of the user's hand into a respective proximal pocket using one hand to guide the drape over the top of the robotic drive and one hand to guide the drape behind the drive. Using mating snap features the user snaps the drape to the back of the drive securing the drape to the back of the robotic drive. Using tabs provided on the drape a user then lifts a portion of the drape up and over the robotic drive housing.

The user then separates the bottom resilient drape plates from the now unfolded folded drape plants and using mating snap features secures a portion of the first resilient member 124 to the bottom of the robotic drive housing and secures a portion of second resilient member 130 to the rear portion of the bottom of the robotic drive housing.

The user then places an upper positioning system portion of the drape over the top of the positioning system. Using straps, the upper positioning portion of the drape is secured to the bottom arm sterile barrier 202 to fully cover the positioning system. In one implementation the positioning system is an articulated arm. While snaps are indicated as some of the attaching features, other coupling methods known in the art are also contemplated. As a non-limiting example, magnets, adhesive tape, hooks and other mechanical, electro-mechanical and chemical coupling may be used in conjunction with or instead of the mechanical snap and hook and loop connectors described herein, Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described is manifestly intended to be as broad as possible. For example, unless specifically otherwise noted, the definitions reciting a single particular element also encompass a plurality of such particular elements.

What is claimed is:

1. A sterile barrier for a robotic drive including a first drive module configured to move along a longitudinal axis of a drive body, the sterile barrier comprising:
   a first resilient member having a first free edge proximate the longitudinal axis, the first free edge adjacent the first drive module being resiliently biased away from and returned to the longitudinal axis as the first drive module moves along the longitudinal axis.

2. The sterile barrier of claim 1, further including a second resilient member having a second free edge proximate the longitudinal axis, wherein the second free edge adjacent the first drive module is resiliently biased away from and returned to the longitudinal axis as the first drive module moves along the longitudinal axis between the first resilient member and the second resilient member.

3. The sterile barrier of claim 2, further including a first rigid member removably coupled to the drive body, wherein the first resilient member is secured to the first rigid member.

4. The sterile barrier of claim 3, further including a flexible drape connected to the first rigid member, the flexible drape covering the drive body.

5. The sterile barrier of claim 4, further comprising:
   a first arm drape member having a C shaped clip removably secured to a portion of an arm supporting the drive body, the first arm drape member including a lower arm drape positioned under the arm, and wherein the flexible drape includes an upper arm drape section covering an upper portion of the arm, wherein the first arm drape member and the upper arm drape section cover an entire surface of the arm.

6. The sterile barrier of claim 4, further including a second rigid member removably coupled to the drive body, wherein the second resilient member is secured to the second rigid member.

7. The sterile barrier of claim 6, wherein the first rigid member includes at least two sections that are in a folded orientation in a packaged configuration and in an unfolded orientation in an install configuration.

8. The sterile barrier of claim 6, wherein the first resilient member includes a first side and an opposing second side, the first side facing the drive body, a portion of the first side of the first resilient member contacting an outer surface of the first drive module as the first drive module moves along the longitudinal axis.

9. The sterile barrier of claim 2, wherein
   the robotic drive includes a second drive module moving along the longitudinal axis of the drive body independently of the first drive module, and
   the first free edge and the second free edge, of the sterile barrier, adjacent the second drive module resiliently move away from the longitudinal axis and back to the longitudinal axis as the second drive module moves along the longitudinal axis.

10. The sterile barrier of claim 9, wherein
    the robotic drive includes a third drive module moving along the longitudinal axis of the drive body independently of the first drive module and the second drive module, and
    the first free edge and the second free edge, of the sterile barrier, adjacent the third drive module resiliently move away from the longitudinal axis and back to the longitudinal axis as the third drive module moves along the longitudinal axis.

11. The sterile barrier of claim 1, wherein the robotic drive includes a first cassette operatively engaging a percutaneous device, the first cassette being releasably secured to the first drive module, wherein the sterile barrier includes a drive module drape secured to the first cassette and removably covering a portion of the first drive module.

12. The sterile barrier of claim 11, wherein the first cassette covers a portion of a first side of the first drive module and the drive module drape covers at least one additional side of the first drive module.

13. The sterile barrier of claim 12, wherein the first cassette and the drive module drape cover substantially all sides of the first drive module.

14. The sterile barrier of claim 11, wherein the drive module drape is a rigid member pivotally attached to the first cassette.

15. The sterile barrier of claim 14, wherein the drive module drape is comprised of a flexible material and is secured to the first cassette.

16. A catheter-based procedure system comprising:
    a robotic drive including a drive body;
    a support arm configured to support the drive body;
    a first drive module and a second drive module configured to move along a longitudinal axis of the drive body; and
    a sterile barrier including
      a first flexible portion covering a portion of the support arm and a portion of the drive body,
      a second portion removably connected to the drive body, the second portion being more rigid than the first flexible, portion, and
      a third resilient portion extending from the second portion, the third resilient portion having a first free edge proximate the longitudinal axis and being adjacent the first drive module, wherein
        the third resilient portion includes a second free edge separate from the first free edge,
        the third resilient portion proximate the longitudinal axis, and the first drive module is configured to move between the first free edge and the second free edge.

17. A method of applying a sterile barrier on a robotic drive having a drive body and a first drive module moving along a longitudinal axis of the drive body, the method comprising:

providing a sterile barrier having a resilient member with a first free edge;

securing the sterile barrier to the drive body and aligning the first free edge of the resilient member along the longitudinal axis of the drive body adjacent a first drive module, the first free edge adjacent the first drive module being resiliently biased away from and returned to the longitudinal axis as the first drive module moves along the longitudinal axis about the robotic drive.

18. The method of claim 17, further comprising:

securing a first cassette to an exposed portion of the first drive module, wherein the first cassette and the sterile barrier cover substantially all sides of the first drive module.

19. The method of claim 18, further comprising:

removably securing a rigid portion of the sterile barrier to the drive body.

\* \* \* \* \*